United States Patent
Vilsmaier et al.

(10) Patent No.: US 6,310,216 B1
(45) Date of Patent: Oct. 30, 2001

(54) SPECIAL 3-AZABICYCLO[3.1.0]HEXANES, METHOD FOR PRODUCING AND MODIFYING THE SAME, AND THEIR USE

(75) Inventors: Elmar Vilsmaier, Otterbach; Torsten Goerz; Gunther Milch, both of Kaiserslautern; Uwe Petersen, Leverkusen; Axel Dalhoff; Gabriele Schmuck, both of Wuppertal, all of (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/463,867
(22) PCT Filed: Jul. 21, 1998
(86) PCT No.: PCT/EP98/04542
§ 371 Date: Feb. 18, 2000
§ 102(e) Date: Feb. 18, 2000
(87) PCT Pub. No.: WO99/06368
PCT Pub. Date: Feb. 11, 1999

(30) Foreign Application Priority Data

Aug. 2, 1997 (DE) .............................. 197 33 439

(51) Int. Cl.[7] ................................................ C07D 209/52
(52) U.S. Cl. ............................................................ 548/452
(58) Field of Search ............................................... 548/452

(56) References Cited

U.S. PATENT DOCUMENTS 5,164,402 * 11/1992 Brighty ................................ 514/300
5,298,629 * 3/1994 Braish .................................. 548/452

OTHER PUBLICATIONS

Tetrahedron, vol. 51, (month unavailable) 1995, Vilsmaier et al, pp. 3507–3520.*

Functionalized Chloroenamines in Aminocyclopropane Synthesis—XVII. [1]3–5–Cyclopiperidine–4–Carboxamides with an unsubstituted 4–Amino Moiety—A Synthetic and a Conformational Study Synlett, Nov. 1996, pp. 1097–1099, Brighty et al, Synthesis of (1α,5α,6α)–6–Amino–3–azabicyclo[3.1.0]hexane, a Novel Achiral Diamine.*

Synthesis, May 1998, Vilsmaier et al., pp. 739–744, Diastereoselective Syntheses of N–Protected Derivatives of 1alpha,5alpha,6beta–6–Amino–3–azabicyclo[3.1.0]hexane; A Route to Trovafloxacin 6beta–Diastereomer, 1998.*

* cited by examiner

Primary Examiner—Robert W. Ramsuer
Assistant Examiner—Sonya N. Wright
(74) Attorney, Agent, or Firm—Joseph C. Gil; Diderico van Eyl; Richard E. L. Henderson

(57) ABSTRACT

6-Amino-3-azabicyclo[3.1.0]hexanes of the formula

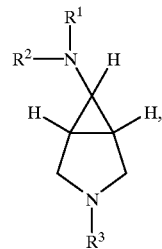

(I)

wherein $R^1$ and $R^2$ independently of one another are $C_3$–$C_4$-alkenyl or Ar—CH(R')— where R' is hydrogen or $C_1$–$C_4$-alkyl and Ar is an optionally substituted $C_6$–$C_{10}$-aryl and $R^3$ is hydrogen, $C_3$–$C_4$-alkenyl, Ar—CH(R')— where R' is hydrogen or $C_1$–$C_4$-alkyl and Ar is an optionally substituted $C_6$–$C_{10}$-aryl or $COOR^4$ where $R^4$ is $C_1$–$C_4$-alkyl or $C_2$–$C_4$-alkenyl. The invention also relates to a method for making these compounds and a method for using them.

1 Claim, No Drawings

SPECIAL 3-AZABICYCLO[3.1.0]HEXANES, METHOD FOR PRODUCING AND MODIFYING THE SAME, AND THEIR USE

This application is a 371 of PCT/EP98/04542 filed of Jul. 21, 1998.

BACKGROUND OF THE INVENTION

The present invention relates firstly to 3-azabicyclo[3.1.0] hexanes with an amino function carrying two protective groups in position 6. The present invention further relates to processes for the preparation of these compounds starting from chloroenamines or bicyclic nitriles, and the modification by cleaving off the protective groups in a customary manner. Finally, the present invention relates to the use of the novel aminioazabicyclohexanes for the preparation of quinolone- and naphthyridinecarboxylic acid derivatives such as 7-(6-amino-3-azabicyclo[3.1.0]hexyl)-6-fluoro-1-(2,4-difluorophenyl)-1,4-dihydro-4-oxo-1,8-naphthyridine-3-carboxylic acid and salts thereof, and optionally to subsequent modification by cleaving off the protective groups.

It is known that 6-amino-3-azabicyclo[3.1.0]hexanes is used as diamine component for the preparation of gyrase inhibitors (cf. WO 91/02526, U.S. Pat. No. 5,164,402, EP-A 413 455, Synlett 1996, 1097. U.S. Pat. No. 5,298,629, WO 93/18001 and Synlett 1996, 1100). In the process, preference is given to using the more readily available 6-exo-amine.

In the syntheses of 6-exo- and 6-endo-amino-3-azabicyclo[3.1.0]hexane to date, the 6-amino group is always obtained alter the cyclopropanation step by converting a functional group. Here, compounds with monoprotected 6-amino groups are used in each case.

In the invention presented below, the amino group is already present in the molecule in the cyclopropanation step. However, the amino group is initially protected by two protective groups, such as, for example, benzyl or allyl radicals, which can be cleaved off later or following incorporation of the novel aminoazabicyclohexanes into quinolone- or naphthyridinecarboxylic acid derivatives. Despite an opposing opinion expressed in the literature (cf. Synlett 1996, 1100), this route is therefore a practical way of also obtaining 6-amino-3-azabicyclo[3.1.0]hexane derivatives having a free amino group in position 6. The starting materials chosen in the novel process are chloroenamines or else bicyclic nitriles preparable therefrom. Chloroenamines give exclusively the 6-endo-amino-3-azabicyclo[3.1.0] hexanes, whilst either 6-endo- or 6-exo-aminio-3-azabicyclo [3.1.0]hexanes are obtainable from the bicyclic nitriles.

The present invention relates to novel 6-amino-3-azabicyclo[3.1.0]hexanes of the formula

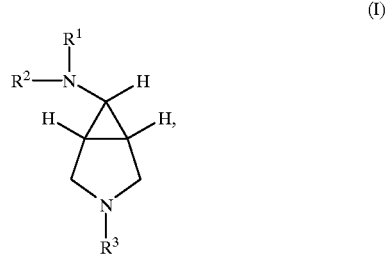

(I)

in which
R$^1$ and R$^2$ independently of one another are C$_3$–C$_4$-alkenyl or Ar—CH(R')— where R'=hydrogen or C$_1$–C$_4$-alkyl and Ar=optionally substituted C$_6$–C$_{10}$-aryl and R$^3$ is hydrogen, C$_3$–C$_4$-alkenyl, Ar—CH(R')— where R'=hydrogen or C$_1$–C$_4$-alkyl and Ar=optionally substituted C$_6$–C$_{10}$-aryl or COOR$^4$ where R$^4$=C$_1$–C$_4$-alkyl or C$_2$–C$_4$-alkenyl.

R' is preferably hydrogen.

The optionally substituted C$_6$–C$_{10}$-aryl can, for example, be unsubstituted C$_6$–C$_{10}$-aryl or C$_6$–C$_{10}$-aryl substituted with from 1 to 3 identical or different substituents. Suitable substituents are, for example, C$_1$–C$_4$-alkyl and C$_1$–C$_4$-alkoxy.

In preferred compounds of the formula (I), R$^1$ and R$^2$ are identical and are allyl or benzyl and R$^3$ is hydrogen, allyl, benzyl, COOCH$_3$ or COOCH=CH$_2$.

The discussed compounds of the formula (I) have two stereoisomers of the formulae

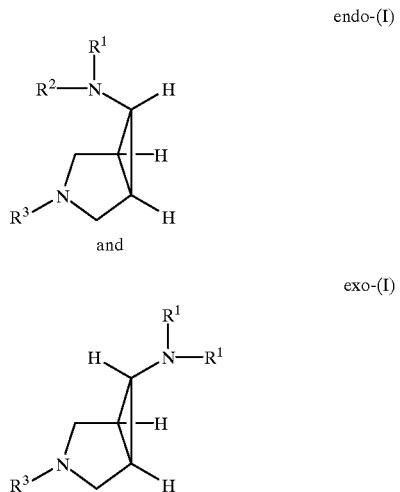

which, should a more accurate name be needed below, are referred to as endo-(I) and exo-(I) respectively. R$^1$, R$^2$ and R$^3$ in the formulae endo-(I) and exo-(I) correspond to the radicals given for formula (I).

The present invention also relates to a process for the preparation of compounds of the formula endo-(I), which is characterized in that a chloroenamines of the formula

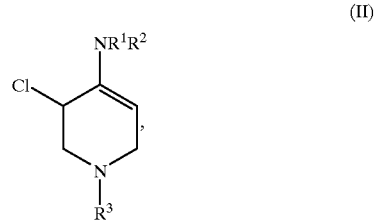

(II)

in which
R$^1$ and R$^2$ are identical and are C$_3$–C$_4$-alkenyl or Ar—CH(R')— where R'=hydrogen or C$_1$–C$_4$-alkyl and Ar=optionally substituted C$_6$–C$_{10}$-aryl, and
R$^3$ has the same scope of meaning as R$^1$ and R$^2$, but can be different from R$^1$ and R$^2$, is reacted with a C$_1$–C$_4$-alkyl alkoxide, to give an N,O-acetal of the formula (III),

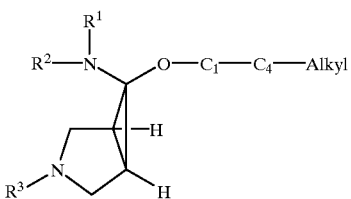

(III)

in which
R¹, R² and R³ are as defined for formula (II),
the latter is treated with a hydride conversion agent, giving an amine of the formula endo-(I)

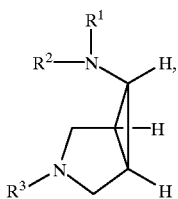

in which
R¹, R² and R³ are as defined above for formula (II).

This process of the present invention is characterized by very high stereoselectivity. The cyclopropane formation from the chloroenamines of the formula (II) and subsequent substitution in the N,O-acetals of the formula (III), which have a tertiary acetalic amine unit, always lead to endo-amine derivatives of the formula endo-(I).

Chloroenamines of the formula (II) can be obtained in a known manner or analogously thereto, for example by reacting 1-[$C_3$–$C_4$-alkenyl or Ar—CH(R') where R'=hydrogen or $C_1$–$C_4$-alkyl and Ar=optionally substituted $C_6$–$C_{10}$-aryl]-4-di-[$C_3$–$C_4$-alkenyl or Ar—CH(R')— where R'=hydrogen or $C_1$–$C_4$-alkyl and Ar=optionally substituted $C_6$–$C_{10}$-aryl-]amino-1,2,5,6-tetrahydropyridine with N-chlorosuccinimide (see Tetrahedron 51, 3507 (1995)).

In the process, the substituted 4-aminotetrahydropyridine used may preferably be 1-benzyl-4-dibenzylamino-1,2,5,6-tetrahydropyridine and 1-benzyl-4-diallylamino-1,2,5,6-tetrahydropyridine. The reaction mixture produced in the chlorination can also be further used as such, i.e. without isolation of the chloroenamines of the formula (II).

The $C_1$–$C_4$-alkyl alkoxides are generally used together with a solvent, preferably in alcoholic solution, for example dissolved in an alcohol which corresponds to the respective alkoxide radical. Preference is given to the sodium methoxide/methanol system, which can be prepared very simply from elemental sodium and excess methanol. Preference is given to using a two- to fourfold molar excess of alkoxide with respect to the chloroenaminie. The reaction often proceeds at a sufficient rate at room temperature. It can be speeded up by heating to e.g. 50 to 60° C.

When reaction with the $C_1$–$C_4$-alkyl alkoxide is complete, the resulting N,O-acetal of the formula (III) can be isolated and purified by, for example, firstly stripping off the solvent, extracting the residue which remains with a solvent, e.g. a hydrocarbon, and isolating the N,O-acetal of the formula (III) from the extract, e.g. by crystallization or distillation under reduced pressure.

Particularly when, during the reaction of a chloroenamines of the formula (II) with a $C_1$–$C_4$-alkyl alkoxide, the chloroenamines of the formula (II) is added as a powder to a solution of a $C_1$–$C_4$-alkyl alkoxide in a $C_1$–$C_4$-alkyl alcohol, the 6-endo-amine isomer of the N,O-acetal [as shown in formula (III)] is exclusively obtained.

Suitable hydride conversion agents for substituting the $C_1$–$C_4$-alkoxy group in the N,O-acetal of the formula (III) by hydrogen are, for example, hydrides, such as lithium aluminium hydride or diisobutyl aluminium hydride. Suitable solvents for this substitution reaction arc, for example, ethers, preference being given to tetrahydrofuran. N,O-acetals of the formula (III) and hydride conversion agents can be used, for example, in a molar ratio of from 1:1.2 to 1:4. The reaction is preferably carried out in a temperature range from, for example, 50 to 70° C. It is generally completed within 3 to 5 hours.

The substitution reaction with the hydride conversion agent can be carried out, for example, by initially introducing the hydride conversion agent suspended in a suitable suspending agent, adding a solution of the N,O-acetal of the formula (III) dropwise, stripping off the suspending agent and solvent after the reaction is complete, hydrolyzing the residues, separating off the solid constituents from the mixture then present, extracting the aqueous phase which remains, and isolating the amine of the formula endo-(I) prepared from the extract.

The solvent used for the N,O-acetal of the formula (III) is preferably the suspending agent for the hydride conversion agent. Suitable for the alkaline hydrolysis is, for example, an aqueous alkali metal hydroxide solution, it being possible, if desired, to pour the reaction mixture into aqueous mineral acid beforehand. Extraction of the aqueous phase can be carried out, for example, using ethers, such as diethyl ether.

Suitable methods for isolating the amine of the formula endo-(I) are, for example, crystallization from a nonpolar solvent, such as pentane, or distillation at reduced pressure.

The present invention also relates to a process for the preparation of compounds of the formula endo-(I), which is characterized in that a chloroenamines of the formula (II)

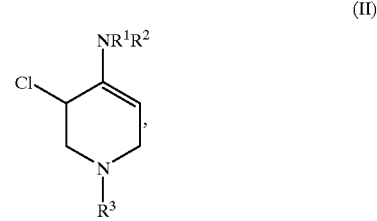

in which
R¹ and R² are identical and are Ar—CH(R')— where R'=hydrogen or $C_1$–$C_4$-alkyl and Ar=optionally substituted $C_6$–$C_{10}$-aryl, and
R³ has the same scope of meaning as R¹ and R², but can be different from R¹ and R²,
is reacted directly with a hydride conversion agent, the resulting primary product is subjected to acidic hydrolysis, and the amine of the formula endo-(I) is liberated by lye. This process likewise proceeds with high stereoselectivity, with the formation of the endo-amine isomers of the formula endo-(I).

This reaction can be carried out, for example, in acetonitrile or an acetonitrile/water mixture (e.g. 9:1 to 2.5:1) with heating to, for example, from 40 to 70° C. Suitable hydride agents are, for example, complex hydrides stable to water and acetonitrile. Sodium borotetrahydride is preferred. Chloroenamines and hydride conversion agents can be used, for example, in a molar ratio from 1:5 to 1:10. The amine adduct formed primarily in the process is cleaved by hydrolysis with acid, preferably hydrochloric acid. The amine of the formula endo-(I) is liberated by subsequently adding lye, e.g. by adding aqueous lye, such as dilute potassium hydroxide solution.

The present invention further relates to a process for the preparation of amines of the formula (I), which is characterized in that a bicyclic nitrile of the formula

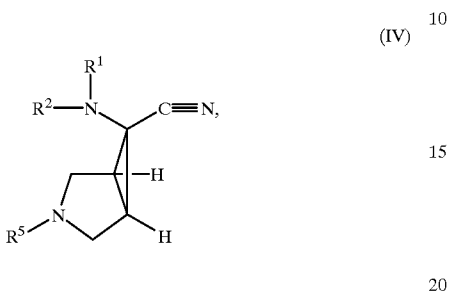

(IV)

in which

R$^1$ and R$^2$ are as defined for formula (I), and

R$^5$ is hydrogen, C$_1$–C$_6$-alkyl, C$_3$–C$_4$-alkenyl, Ar—CH(R')— where R'=hydrogen or C$_1$–C$_4$-alkyl and Ar=optionally substituted C$_6$–C$_{10}$-aryl or COOR$^4$ where R$^4$=C$_1$–C$_4$-alkyl or C$_2$–C$_4$-alkenyl, is reacted with an alkali metal in liquid ammonia, optionally in the mixture with a mono- or dialkylamine. The alkyl groups of these amines preferably contain from 1 to 4 carbon atoms. Preference is given to using ethylamine. This process can be used to stereoselectively prepare 6-amino-3-azabicyclo[3.1.0]hexane derivatives of the formula endo-(I) and exo-(I), in which R$^1$ and R$^2$ are as defined for formula (I), and R$^3$ is hydrogen, C$_1$–C$_6$-alkyl, C$_3$–C$_4$-alkenyl, Ar—CH(R')— where R'=hydrogen or C$_1$–C$_4$-alkyl and Ar=optionally substituted C$_6$–C$_1$C$_{10}$-aryl or COOR$^4$ where R$^4$=C$_1$–C$_4$-alkyl or C$_2$–C$_4$-alkenyl.

Bicyclic nitriles of the formula (IV) are obtainable, for example, in accordance with Tetrahedron 51, 3507 (1995) from chloroenamines or analogously to the procedure described therein. According to the invention, the nitrile group in the nitrile of the formula (IV) can be replaced by hydrogen with an alkali metal in liquid ammonia or in a mixture of ammonia and a mono- or dialkylamine, preferably ethylamine.

For the reaction, the nitrile and the alkali metal can be reacted in a molar ratio of, for example, from 1:3 to 1:8. Preference is given to a ratio of from 1:5 to 1:7. Per mmol of nitrile of the formula (IV), it is possible to use, for example, from 15 to 100 ml, preferably from 15 to 25 ml, of ammonia or alkylamine/ammonia mixture. The temperature used plays an important role for the stereochemical progress of the reaction. Carrying out the reaction at from −70° C. to −40° C. effects substitution with complete or almost complete retention of the configuration on the C(6), with formation of the 6-endo-amine isomers of the formula endo-(I). If, on the other hand, the analogous reaction of a nitrile of the formula (IV) where R$^1$=R$^2$ benzyl and R$^5$=hydrogen is carried out in a mixture of ethylamine and ammonia at ±0° C. using sodium or, preferably, lithium as alkali metal, then a stereoisomer mixture of amines of the formula exo-(I) and endo-(I) where R$^1$=R$^2$=benzyl and R$^3$=hydrogen is obtained. The 6-exo-amine isomer of the formula exo-(I) mentioned is generally present in an amount of (80±10)%; it can be obtained as pure compound by crystallization or other separation methods. It corresponds to a 3-azabicyclo[3.1.0] hexane with an amine group carrying two protective groups in position 6-exo; this is a derivative of the diamine building block in the gyrase inhibitor described in the introduction.

The present invention further includes the modification of the bicyclic compounds, obtained via chloroenamines of the formula (II) or from nitrites of the formula (IV), of the formula

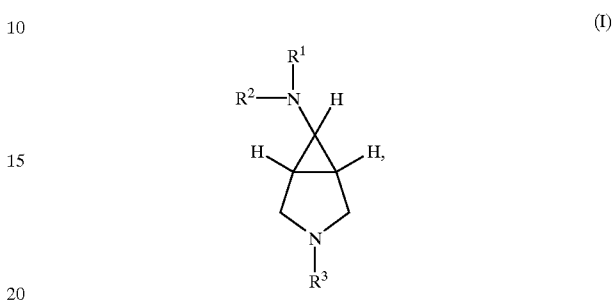

(I)

where R$^1$, R$^2$ and R$^3$ can be as defined for formulae (II) and (IV), by cleaving off the protective groups in formulae II and IV in a customary manner.

Suitable reactions for cleaving off the protective groups from an amine of the formula (I) are, for example, a hydrogenating treatment, reaction with chloroformic C$_2$–C$_4$-alkenyl esters and subsequent acidic hydrolysis, reaction with chloroformic C$_1$–C$_4$-alkyl ester to give an urethane and its cleavage with halogenotrialkylsilane or deallylation with tetrakis(triaryl)phosphinepalladium and a CH acid, such as N,N'-di-alkylbarbituric acid.

The hydrogenating treatment can be carried out, for example, with hydrogen in the presence of a noble metal catalyst. Suitable catalysts are, for example, elemental palladium, in particular elemental palladium on a support such as carbon, aluminium oxide, silicon dioxide or silicates. The hydrogenating treatment can likewise be carried out in a solvent. Suitable solvents for this purpose are, for example, alcohols such as methanol, to which tertiary amines, such as triethylamine, can optionally be added. The other reaction conditions for this hydrogenating treatment (e.g. pressure, temperature etc.) and for working-up the reaction mixture produced can be chosen in ways known for such reactions from the prior art. According to these methods, it is possible, for example in the amine of the formula endo-(I) where R$^1$=R$^2$=R$^3$=benzyl, to reductively remove all benzyl groups by hydrogen. This produces an amine of the formula

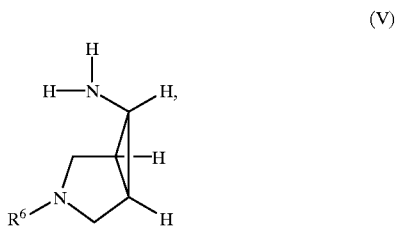

(V)

in which

R$^6$ is hydrogen.

Selective removal of the N(3)-CH(R')—Ar group in an amine of the formula (I) can, for example, take place by reacting with chloroformic aceto-C$_2$–C$_4$-alkenyl ester and subsequent acidic hydrolysis of the resulting urethane. Particularly suitable for this purpose are a benzyl group on N(3)

in the amine and vinyl chloroformate. This conversion to the urethane is preferably carried out in a solvent. Examples are dichloromethane, chloroform and acetonitrile, chloroform being preferred. Vinyl chloroformate and amine can be used, for example, in the molar ratio of (1.1 to 1.2):1. Reaction temperatures in the range from 40 to 60° C. and reaction times from 1 to 3 hours generally lead to good results. Separating off the coproduct benzyl chloride and purifying the urethane can be carried out by distillation under reduced pressure. Under the conditions described, dibenzylamine hydrochloride is formed as a by-product. Cleaving off the vinyloxycarbonyl group in the urethane, e.g. with concentrated hydrochloric acid in chloroform, and working up with lye gives the partially deprotected amine of the formula (I). In these methods, it is possible, for example, in an amine of the formula endo-(I) in which $R^1=R^2=R^3$=benzyl, to selectively replace the benzyl radical $R^3$ by hydrogen.

Selective removal of the N(3)-CH(R')—Ar group in an amine of the formula (I) can also be carried out by reaction with chloroformic $C_1$–$C_4$-alkyl esters and subsequent reaction with a halogenotrialkylsilane. Particularly suitable for this purpose are a benzyl group on N(3) in the amine and methyl chloroformate, and cleavage of the resulting urethane with trimethylsilyl iodide. The reaction to give the urethane is preferably carried out in a solvent. Examples are dichloromethane and chloroform in a mixture with pyridine. Chloroform/pyridine in a ratio of (4 to 6):1 is preferred. Methyl chloroformate and amine can be reacted, for example, in a molar ratio of (1.5 to 2):1. Reaction temperatures in the range from 40 to 60° C. and reaction times from 3 to 6 hours generally lead to good results. Separating off the coproduct benzyl chloride and purifying the urethane can be carried out by distillation under reduced pressure. Under the described conditions, dibenzylamino hydrochloride is formed as by-product. Cleaving off the methoxycarbonyl group in the urethane with halogeno-trialkylsilane, in particular trimethylsilyl iodide, is preferably carried out in solvent, such as chloroform, at from 40 to 70° C., preferably at from 50 to 65° C. Halogeno-trialkylsilane can be used, for example, in a 4- to 6-fold molar excess. As a rule, the reaction is complete after 5 to 8 hours. It is then expedient to carry out acid hydrolysis. In this connection, good results are achieved using methanolic hydrogen chloride solution. Working up with lye then releases the amine of the formula (I). In these methods, it is possible, for example in an amine of the formula endo-(I) in which $R^1=R^2=R^3$=benzyl, to selectively replace the benzyl radical $R^3$ by hydrogen. Alternatively, it is possible, for example, to also debenzylate the resulting urethane of the formula endo-(I) where $R^1=R^2=$benzyl and $R^3=COOCH_3$ to give the amine of the formula (V) where $R^6=COOCH_3$.

For the deallylation, the compound of the formula (I) where $R^1$ and $R^2=C_3$–$C_4$-alkenyl is, for example, reacted with N,N'-dimethylbarbituric acid or a similar compound and tetrakis(triphenylphosphine)palladium or an analogous derivative, preferably in a molar ratio of 1:(3 to 4):(0.01 to 0.05). It is also possible to choose these molar ratios differently. Suitable solvents for this purpose are, for example, chlorinated hydrocarbons, such as methylene chloride. Thus, the diallyl compound of the formula endo-(I) where $R^1=R^2$=allyl and $R^3$=benzyl can, for example, be deallylated in the presence of, for example, tetrakis(triphenylphosphine)palladium using N,N'-dimethylbarbituric acid to give the monobenzyl compound of the formula (V) There $R^6$=benzyl. The reaction is preferably carried out in dichloromethane at, for example, from 30 to 40° C. Preference is given to using the starting material N,N'-dituethylbarbituric acid and tetrakis(triphentylphosphine)palladium, in a ratio of 1:(3.0 to 3.5):(0.01 to 0.03).

In all reactions which proceed with removal of benzyl or allyl protective groups, the configuration on the C(6) of the 3-aza-bicyclo[3.1.0]hexane system is not changed.

The present invention also relates to the use of the novel compounds of the formula (I) for the preparation of quinolone- and naphthyridinecarboxylic acid derivatives with optional subsequent modification of the 6-amino radical by cleaving off the protective groups. Thus, for example, 7-(6-endo-amino-3-azabicyclo[3.1.0]hex-3-yl)-6-fluoro-1-(2,4-difluorophenyl)-1,4-dihydro-4-oxo-1,8-naphthyridine-3-carboxylic acid and salts thereof in particular are accessible. In this connection, it is possible, for example, to proceed in accordance with the following equation.

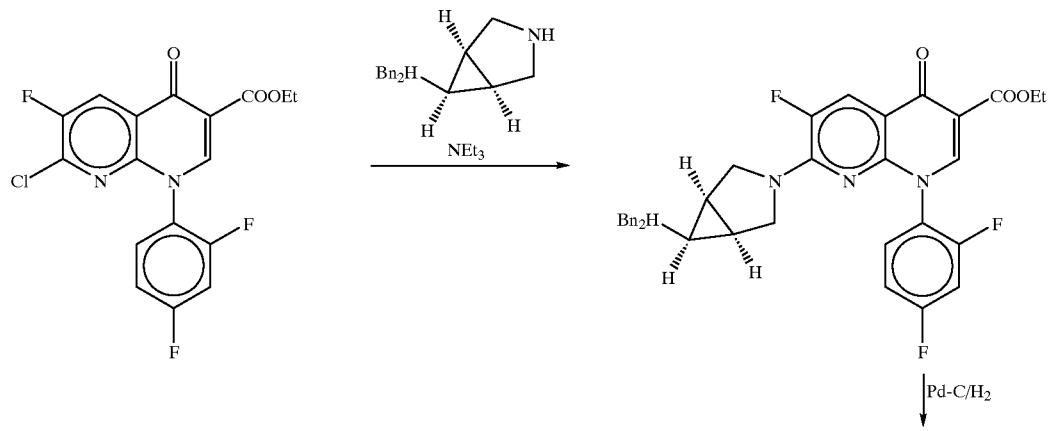

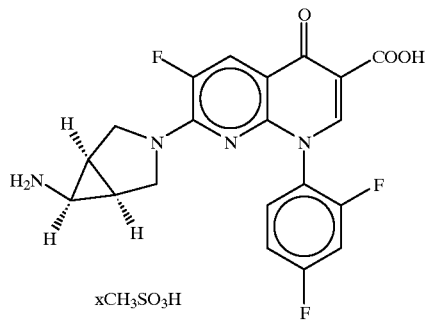

xCH₃SO₃H

Bn = benzyl
Et = ethyl

-continued

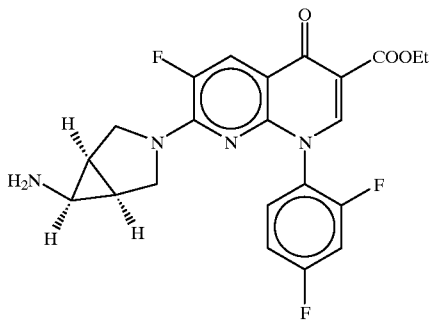

CH₃SO₃H/H₂O 7-(6-Endo-amino-3-azabicyclo[3.1.0]hex-3-yl)-6-fluoro-1-(2,4-difluorophenyl)-1,4-dihydro-4-oxo-1,8-naphthyridine-3-carboxylic acid and its salts are characterized, in contrast to the corresponding 6-exo-amine isomers, by significantly lower neurotoxicity. According to an analogous equation, it is also possible to prepare, from the novel 6-exo-amine isomers of the formula exo-(I) where $R^1=R^2$=benzyl and $R^3$=H, 7-(6-exo-amino-3-azabicyclo[3.1.0]hex-3-yl)-6-fluoro-1-(2,4-difluorophenyl)-1,4-dihydro-4-oxo-1,8-naphthyridine-3-carboxylic acid and its salts.

The invention is further described in the following illustrative examples in which all parts and percentages are by weight unless otherwise indicated.

EXAMPLES

Example 1

A solution of 4.14 g of N-chlorosuccinimide in 200 ml of dichloromethane was added dropwise to a solution of 11.42 [lacuna] of 1-benzyl-4-dibenzylamino-1,2,5,6-tetrahydripyridine in 50 ml of dichloromethane at −78° C. over the course of 2 hours. The mixture was then stirred for 1 hour at −78° C. Stirring was then continued with slow warming to −30° C. for 2 hours. Following removal of the solvent under a high vacuum, the residue was extracted with 5×150 ml of pentane. The chloroenamines of the formula (II) where $R^1=R^2=R^3$=benzyl precipitated out from the pentane solution at low temperature as colourless powder, giving 10.9 g, which corresponds to a yield of 87% of theory. The melting point was 57° C.

$^1$H-NMR spectrum: 2.67 ppm ($H_{B1}$, 1H), 2.95 ppm ($H_{B2}$, 1H), 3.08 ppm ($H_{A1}$, 1H), 3.39 ppm ($H_{A2}$, 1H), 4.68 ppm ($H_{X1}$, $H_{X2}$, 2H) (2 ABX systems), 3.52 ppm ($H_{B3}$, 1H), 3.82 ppm ($H_{A3}$, 1H) (AB system), 4.10 ppm ($H_{B4}$, 2H), 4.43 ppm ($H_{A4}$, 2H) (AB system), 7.15–7.45 ppm (m, 15H).

$^{13}$C-NMR spectrum: 141.1 (s), 138.7 (s), 137.6 (s), 128.9 (d), 128.3 (d), 128.2 (d), 127.3 (d), 127.0 (d), 126.8 (d), 101.1 (d), 61.5 (t), 57.4 (t), 54.3 (d), 52.49 (t), 52.46 (t).

Example 2

4.5 ml of titanium tetrachloride mixed with 15 ml of toluene were added, at 0° C., to a solution of 41.84 ml of diallylamine and 15 ml of N-benzylpiperidone in 200 ml of toluene. The mixture was stirred for 1 hour at 0° C. and for 20 hours at 20° C. The solid residue was then filtered off with suction. After evaporating off the solvent under reduced pressure and distilling the residue in a Kugelrohr at 130–150° C./1.3·10⁻³ mbar, the filtrate gave the corresponding enamine as a pale yellow oil (13.03 g) in 96% purity. A solution of 6.22 g of N-chlorosuccinimide in 160 ml of dichloromethane was added dropwise with stirring at −78° C. over the course of 2 hours to the solution of the oil isolated in this manner in 20 ml of dichloromethane. The mixture is stirred for a further hour at −78° C. and then for 4 hours with warming to −50° C. The solvent was then evaporated off under reduced pressure, and the residue was extracted with 7×50 ml of pentane. The cooled pentane solution gave 12.92 g of chloroenamines of the formula (II) where $R^1=R^2$=allyl and $R^3$=benzyl having a melting point of 34° C. This corresponds to a yield of 50% of theory, based on N-benzylpiperidone used.

$^1$-NMR spectrum: 2.64 ppm ($H_{B1}$, 1H), 2.94 ppm ($H_{B2}$, 1H), 3.07 ppm ($H_{A1}$, 1H), 3.44 ppm ($H_{A2}$, 1H), 4.55 ppm ($H_{X1}$, 1H), 4.62 ($H_{X2}$, 1H) (2 ABX systems), 3.52 ppm ($H_{B3}$, 1H), 3.79 ppm ($H_{A3}$, 1H) (AB system), 3.58 ppm ($H_Y$, 2H), 3.78 ppm ($H_{X3}$, 2H), 5.10 ppm ($H_M$, 1H), 5.13 ppm ($H_N$, 1H), 5.78 ppm (HA₄, 1H) (AMNXY system), 7.22–7.43 ppm (m, 5H).

$^{13}$C-NMR spectrum: 140.5 (s), 137.5 (s), 134.7 (d), 128.6 (d), 127.9 (d), 126.8 (d), 116.1 (t), 99.3 (d), 61.3 (t), 57.2 (t), 54.0 (d), 52.4 (t), 51.0 (t).

Example 3

4.00 g of the chloroenamines obtained as in Example 2 were added to a solution of sodium methoxide in methanol, which had been prepared from 0.91 g of sodium and 80 ml of methanol. The mixture was stirred for 3 days at 20° C., then the methanol was evaporated under reduced pressure. The residue was extracted with pentane, and the extract was distilled in a Kugelrohr at 130° C./1.3·10⁻³ mbar. 3.35 g of the N,O-acetal of the formula (III) where $R^1=R^2$=allyl, $R^3$=benzyl and $C_1-C_4$-alkyl=methyl were obtained as colourless oil. This corresponded to a yield of 85% of theory.

$^1$H-NMR spectrum: 2.01 ($H_{X1}$, $H_{X'1}$, 2H), 2.32 ($H_{A1}$, $H_{A'1}$, 2H), 3.07 ($H_{B1}$, $H_{B'1}$, 2H) (AA'BB'XX' system), 3.29 (s, 3H), 3.58 (s, 2H), 3.50 ($H_{X2}$, 4H), 5.14 ($H_M$, 1H), 5.16 ($H_N$, 1H), 5.89 ($H_{A2}$, 1H) (AMNX₂ system), 7.22–7.31 (m, 5H).

$^{13}$C-NMR spectrum: 139.1 (s), 136.1 (d), 128.3 (d), 126.4 (d), 116.5 (t), 87.2 (s), 58.9 (t), 54.5 (q), 53.28 (t), 53.18 (t), 33.7 (d).

Example 4 a) A solution of 1.77 g of N-chlorosuccinimide in 80 ml of dichloromethane was added dropwise, at −78° C. over the course of 2 hours, to a solution of 4.88 g of 1-benzyl-4-dibenzylamino-1,2,5,6-tetrahydripyridine in 20 ml of dicloromethane. The mixture was further stirred for a further 4 hours with slow warming to −50° C. The solvent was then removed under reduced pressure. A sodium methoxide solution prepared from 1.22 g of sodium and 100 ml of methanol was added to the residue. After the mixture had been stirred for 20 hours at room temperature, the solution was removed under a high vacuum. The residue was extracted with 4×40 ml of pentane to give 4.17 g of N,O-acetal of the formula (III) where $R^1=R^2=R^3$=benzyl and $C_1$–$C_4$-alkyl=methyl, which crystallized upon storage in a freezer. The product had a melting point of 69° C. and had been obtained in a yield of 79% of theory.

b) 3.83 g of the chloroenamines obtained as in Example 1 were reacted analogously to Example 3, giving 3.59 g of the same N,O-acetal as in Example 4a. This corresponded to a yield of 95% of theory.

$^1$H-NMR spectrum: 1.90 ppm ($H_X$, $H_{X'}$, 2H), 2.37 ppm ($H_{A1}$, $H_{A'1}$, 2H), 2.71 ppm ($H_{B1}$, $H_{B'1}$, 2H) (AA'BB'XX'system), 3.33 ppm (s, 3H), 3.59 ppm (s, 2H), 3.93 ppm ($H_{B2}$, 2H), 4.12 ppm ($H_{A2}$, 2H) (AB system), 7.19–7.29 ppm, 7.39–7.41 ppm (m, 15H).

$^{13}$C-NMR spectrum: 139.1 (s), 138.5 (s), 129.1 (d), 128.4 (d), 127.7 (d), 127.4 (d), 126.4 (d), 126.3 (d), 85.0 (s), 59.4 (t), 55.3 (t), 55.0 (q), 52.9 (t), 32.7 (d).

Example 5 a) A solution of 2.1 g of the N,O-acetal obtained as in Example 4 in 25 ml of tetrahydrofuran was slowly added dropwise to a suspension of 0.25 g of lithium aluminium hydride in 5 ml of tetrahydrofuran. The mixture was stirred for 4 hours at 60° C. The solvent was then removed under reduced pressure, and the residue was carefully hydrolysed with ice cooling by adding 30 ml of 2 molar aqueous potassium hydroxide solution. After the solid components had been centrifuged off, the aqueous phase was extracted with 4×20 ml of ether and the residue was extracted with 20 ml of diethyl ether. Following removal of the solvent and crystallization from pentane, the combined extracts gave 1.65 g of an amine of the formula endo-(I) where $R^1=R^2=R^3$=benzyl having a melting point of 75° C. This corresponded to a yield of 85% of theory.

$^1$H-NMR spectrum: 1.73 ppm ($H_X$, $H_{X'}$, 2H), 2.01 ppm ($H_Y$, 1H), 2.42 ppm ($H_A$,$H_{A'}$, 2H), 2.95 ppm ($H_B$, $H_{B'}$, 2H) (AA'BB'XX'Y system), 3.59 ppm (s, 4H), 3.68 ppm (s, 2H), 7.19–7.37 ppm (m, 15H).

$^{13}$C-NMR spectrum: 139.6 (s), 137.5 (s) 129.6 (d), 128.8 (d), 128.1 (d), 127.9 (d), 126.8 (d), 126.7 (d), 59.4 (t), 56.1 (t), 51.8 (t), 47.5 (d), 25.8 (d).

b) In an analogous manner, 5.0 g of N,O-acetal, which had been obtained as in Example 3, and 2.54 g of lithium aluminium hydride in 90 ml of tetrahydrofuran gave 3.01 g of an amine of the formula endo-(I) where $R^1=R^2$=allyl and $R^3$=benzyl as colourless oil having a boiling point of 115° C./1.3·10$^{-3}$ mbar. This corresponded to a yield of 67% of theory.

$^1$H-NMR spectrum: 1.72 ppm ($H_X$, $H_{X'}$, 2H), 2.11 ppm ($H_Y$, 1H), 2.35 ppm ($H_A$,$H_{A'}$, 2H), 3.10 ppm ($H_B$, $H_{B'}$, 2H) (AA'BB'XX'Y system), 3.61 ppm (s, 2H), 3.16 ppm ($H_{X2}$, 4H), 5.15 ppm ($H_M$, 1H), 5.18 ppm ($H_N$, 1H), 5.92 ppm ($H_{A2}$, 1H) (AMNX$_2$ system), 7.20–7.35 ppm (m, 5H).

$^{13}$C-NMR spectrum: 139.7 (s), 134.7 (s) 128.4 (d), 127.9 (d), 126.4 (d), 117.1 (t), 58.7 (t), 55.1 (t), 51.8 (t), 46.9 (d), 25.6 (d).

Example 6

1.88 ml of 1 molar diisobutylaluminium hydride solution in tetrahydrofuran were added dropwise to a solution of 0.5 g of N,O-acetal, which had been obtained as in Example 4, in 30 ml of tetrahydrofuran. The solution was stirred for 5 hours at 60° C. and for a further 3 days at room temperature and then poured onto a mixture of 20 g of ice, 40 ml of water (40 ml) and 1 ml of 96% strength sulphuric acid. Then, with ice cooling, 30 ml of a 3 molar aqueous potassium hydroxide solution were added, the aqueous phase was extracted with 5×25 ml of diethyl ether, and the ether phase was dried over magnesium sulphate. Removal of the solvent, Kugelrohr distillation of the residue (130° C./1.3·10$^{-3}$ mbar) and crystallization of the distillate from pentane gave 0.41 g of an amine of the formula endo-(I) wehre $R^1=R^2=R^3$=benzyl having a melting point of 75° C. This corresponded to a yield of 89% of theory.

Example 7 a) A solution of 0.5 ml of vinyl chloroformate in 5 ml of chloroform was added dropwise, at 50° C. over the course of 15 minutes, to a solution of 1.95 g of the product from Example 5 in 80 [lacuna] chloroform. The mixture was stirred for 1.5 hours at 50° C. and for 2 hours at room temperature. The solvent was then removed under reduced pressure, and the residue was distilled in a rotating Kugelrohr at 140 to 180° C./1.3·10$^{-3}$ mbar. The distillate was extracted with 4×20 ml of pentane, and the combined extracts were distilled again, ultimately at 135° C./1.3·10$^{-3}$ mbar. This gave 0.93 g of an amine of the formula endo-(I) in which $R^1=R^2$=benzyl and $R^3$=COOCH=CH$_2$. This corresponded to a yield of 50% of theory.

$^1$H-NMR spectrum: 1.70 ppm ($H_X$, $H_Y$, 2H), 2.09 ppm ($H_Z$, 1H), 3.39 ppm ($H_A$, 1H), 3.49 ppm ($H_C$, 1H), 3.51 ppm ($H_B$, 1H), 3.56 ppm ($H_D$,1H) (ABCDXYZ system), 3.60 ppm (s, 4H), 4.45 ppm (dd, 1H), 4.76 ppm (dd, 1H), 7.20–7.36 ppm (m, 11H).

$^{13}$C-NMR spectrum: 150.9(s), 142.4(d), 137.2(s), 129.4 (d), 128.1 (d), 127.0 (d), 94.7 (dd), 57.7 (t), 46.0 (t), 45.2 (t), 43.4 (d), 23.2 (d), 22.4 (d).

b) In an analogous manner, 0.5 g of the product from Example 5 and 0.18 ml of methyl chloroformate in a mixture of 15 ml of chloroform and 3 ml of pyridine gave a product of the formula endo-(I) in which $R^1=R^2$=benzyl and $R^3$=COOCH$_3$. The yield was 0.21 g, which corresponded to 46% of theory.

$^1$H-NMR spectrum: 1.70 ppm ($H_X H_Y$, 2H), 2.09 ppm ($H_Z$, 1H), 3.37 ppm ($H_A$, 1H), 3.46 ppm ($H_B$, 1H), 3.52 ppm ($H_C$, 1H), 3.55 ppm ($H_D$, 1H) (ABCDXYZ system), 3.61 ppm (s, 4H), 3.74 ppm (s, 3H), 7.22–7.34 ppm (m, 10 H).

$^{13}$C-NMR spectrum: 154.5 (s), 137.3 (s), 129.5 (d), 128.1 (d), 127.0 (d), 57.3 (t), 52.1 (q), 46.0 (t), 45.2 (t), 43.2 (d), 23.4 (d), 22.7 (d).

Example 8

7 ml of 37% strength aqueous hydrochloric acid were added to a solution of 0.93 g of the product obtained as in Example 7a) in 30 ml of chloroform, and the mixture was stirred for 14 hours at room temperature. 20 ml of water were then added and the chloroform was removed under reduced pressure. The aqueous solution was extracted by shaking with 20 ml of diethyl ether, and then, with ice cooling, 25 ml of aqueous, 5 molar potassium hydroxide solution were added. The reaction product was extracted from the basic solution with 80 ml of diethyl ether in a Kutscher-Steudel apparatus (see Römpp Chemie-Lexikon, 9th edition on CD-ROM, version 1.0 (1995)) for 5 days. Kugelrohr distillation of the extract at 105° C./1.3·10$^{-3}$ mbar and crystallization of the distillate from pentane gives 0.55 g of pure product of the formula endo-(I) where $R^1=R^2=$ benzyl and $R^3=$hydrogen. This corresponded to a yield of 74% of theory. The product had a melting point of 86° C.

$^1$H-NMR spectrum: 1.45 ppm ($H_X$, $H_{X'}$, 2H), 1.98 ppm ($H_Y$, 1H), 2.52 ppm ($H_A$, $H_{A'}$, 2H), 2.78 ppm ($H_B$, $H_{B'}$, 2H) (AA'BB'XX'Y system), 1.85 ppm (s, broad, 1H), 3.55 ppm (s, 4H), 7.22–7.35 ppm (m, 10H).

$^{13}$C-NMR spectrum: 138.2 (s), 129.5 (d), 128.2 (d), 127.1 (d), 59.7 (t), 48.3 (t), 45.0 (d), 24.5 (d).

Example 9

A solution of 0.21 ml of iodotrimethylsilane and 0.10 g of the product from Example 7b) in 5 ml of chloroform was stirred at 60° C. for 6.5 hours. Then at 20° C., 2 ml of a concentrated methanolic hydrogen chloride solution were added. After the mixture had been stirred for 10 minutes, a solution of 0.65 g of sodium methoxide in 20 ml of methanol was added. Removal of the solvent under reduced pressure followed by the addition of 10 ml of aqueous 2-normal potassium hydroxide solution gave the free base, which was obtained in pure form by extraction with 5×20 ml of diethyl ether and distillation in a Kugelrohr at 105° C./1.3·10$^{-3}$ mbar. This results in 0.07 g of a product of the formula endo-(I) where $R^1=R^2=$benzyl and $R^3=$hydrogen. This corresponded to a yield of 85% of theory.

Example 10

A solution of 0.13 g of the starting material also used in Example 9 in 14 ml of diethyl ether/chloroform mixture (1:1) was converted into the ammonium salt using hydrogen chloride and, following evaporation of the solvent, the salt was isolated. A solution of the ammonium salt obtained following evaporation of the solvent in 30 ml of methanol was debenzylated with hydrogen in the presence of 0.1 g of Pd/C catalyst (10% Pd). The catalyst was then filtered off, and the solvent was removed under reduced pressure. Treatment of the residue with 0.65 g of sodium carbonate and distillation of the mixture in a Kugelrohr at 150° C./1.3·10$^{-3}$ mbar gave the diamine of the formula (V) where $R^6=$COOCH$_3$. This was purified by sublimation at 70° C./1.3·10$^{-3}$ mbar. 0.04 g of the diamine having a melting point of 76° C. were obtained. This corresponded to a yield of 66% of theory.

$^1$H NMR spectrum: 1.60 ppm ($H_X$, $H_Y$, 2H), 2.48 ppm ($H_Z$, 1H), 3.46 ppm, 3.53 ppm ($H_A/H_C$, 2H), 3.56 ppm, 3.62 ppm ($H_B/H_D$, 2H), (ABCDXYZ system), 3.68 ppm (s, 3H).

$^{13}$C-NMR spectrum. 154.6 (s), 52.2(q), 44.9 (t), 44.3 (t), 31.4 (d), 21.3 (d), 20.4 (d).

Example 11

A solution of 1.86 g of the product obtained as in Example 5b in 9 ml of dichloromethane was added to a mixture of 0.16 g of tetrakis(triphenylphosphine)palladium and 3.49 g of N,N'-dimethylbarbituric acid, and the mixture was stirred for 5 hours at 40° C. The solvent was then evaporated. 40 ml of concentrated aqueous sodium carbonate solution were then added to the residue, and the mixture was extracted with 3×40 ml of diethyl ether. 35 ml of a 2-molar aqueous hydrochloric acid solution were added to the ether extract, the ether was evaporated and the residue was washed with 3×30 ml of ethyl acetate. Pure amine hydrochloride was left behind. The addition of 10.6 g of sodium carbonate, extraction with 5×30 ml of diethyl ether and distillation of the extract in a Kugelrohr at 70° C./1.3·10$^{-3}$ mbar gave 0.9 g of free base of the formula (V) where $R^6=$benzyl. This corresponded to a yield of 69% of theory.

$^1$H-NMR spectrum: 1.37 ppm ($H_X$, $H_{X'}$, 2H), 2.35 ppm ($H_Y$, 1H), 2.65 ppm ($H_B$, $H_{B'}$, 2H), 3.05 ppm ($H_A$, $H_{A'}$, 2H), (AA'BB'XX'Y system), 1.92 ppm (s, broad, 2H), 3.59 ppm (s, 2H), 7.20–7.31 ppm (m, 5H).

$^{13}$C-NMR spectrum: 139.4 (s), 128.2 (d), 128.1 (d), 126.7 (d), 59.8 (t), 52.5 (t), 34.5 (d), 19.9(d).

Example 12 a) 2 g of finely powdered 3-benzyl-6-dibenzylamino-3-azabicyclo[3.1.0]bicyclohexane-6-carbonitrile were added in one portion and with vigorous stirring to a solution, cooled to −78° C., of 0.7 g of sodium in 100 ml of liquid ammonia. The cooling bath was then removed, and the mixture was further stirred until the ammonia had completely evaporated. The residue which remained was extracted with 3×30 ml of diethyl ether and the combined extracts were distilled in a Kugelrohr at 190° C./7·10$^{-3}$ mbar. Distillation gave 1.76 g of a diamine of the formula endo-(I) where $R^1=R^2=R^3=$benzyl as clear, pale yellow oil, which subsequently crystallized. The crystalline substance of melting point from 72 to 74° C. obtained in this way corresponded to a yield of 94% of theory.

b) In an analogous manner, 2.0 g of 6-endo-dibenzylamino-3-azabicyclo[3.1.0]hexane-6-carbonitrile and 0.7 g of sodium in 100 ml of liquid ammonia were reacted to give 6-endo-dibenzylamino-3-azabicyclo[3.1.0]hexane. The resulting crude product (1.61 g) was purified by distillation under a high vacuum. 1.09 g of a fraction were obtained from 115 to 150° C./7·10$^{-3}$ mbar, which was pure 6-endo-dibenzylamino-3-azabicyclo[3.1.0]hexane of the formula endo-(I) where $R^1=R^2=$benzyl and $R^3=$hydrogen. This corresponded to a yield of 60% of theory.

c) In an analogous manner, 1.5 g of 6-endo-dibenzylamino-3-methyl-3-azabicyclo[3.1.0]hexane-6-carbonitrile and 0,65 g of sodium in 60 ml of liquid ammonia were reacted to give 6-endo-dibenzylamino-3-methyl-3-azabicyclo[3.1.0]hexane. The resulting crude product (1.4 g) was purified by distillation under a high vacuum. 0.96 g of a fraction were obtained from 130 to 150° C./7·10$^{-3}$ mbar, which was pure 6-endo-dibenzylamino-3-methyl-3-azabicyclo[3.1.0]hexane of the formula endo-(I) where $R^1=R^2$ benzyl and $R^3=$methyl. This corresponded to a yield of 70 of theory.

$^1$H-NMR spectrum: 1.80 ppm ($H_X$, $H_{X'}$, 2H), 2.03 ppm ($H_Y$, 1H), 2.33 ppm ($H_A$, $H_{A'}$, 2H), 3.02 ppm ($H_B$, $H_{B'}$, 2H), (AA'BB'XX'Y system), 2.34 ppm (s, 3H), 3.60 ppm (s, 4H), 7.25–7.36 ppm (m, 10H).

$^{13}$C-NMR spectrum: 137.9 (s), 130.2 (d), 128.6 (d), 127.5 (d), 56.5 (t), 54.1 (t), 48.2 (d)m 41.3 (q), 27.3 (d).

Example 13

Ammonia was passed, at −78° C, into a mixture of 20 ml of ethylamine and 0.14 g of lithium. When the mixture started to develop a blue coloration, the ammonia feed was stopped, and the mixture was stirred at this temperature until the lithium had completely dissolved. The solution was then warmed to 0° C. After excess ammonia had been evaporated, 40 ml of ethylamine and 1.0 g of 6-endo-dibenzylamino-3-azabicyclo[3.1.0]hexane-6-carbonitrile were added. A colour change from red to yellow-green indicates the end of the reductive debenzylation. Excess lithium was then destroyed by adding ammonium chloride. After the solvent had been evaporated, extraction of the residue with 3×30 ml of diethyl ether and distillation of the extract at 100 to 150° C./7·10$^{-3}$ mbar in a Kugelrohr gave 0.70 g of 6-dibenzylamino- 3-azabicyclo[3.1.0]hexane diastereomer mixture. This corresponded to a yield of 75%o of theory. The mixture consisted of 80% of exo-amine and 20% endo-amine. 0.51 g of the pure exo-diastereomer of the formula exo-(I) where $R^1=R^2$=benzyl and $R^3$=hydrogen were obtained from the ether extracts following evaporation of the diethyl ether and crystallization of the residue from pentane. This corresponded to a yield of 56% of theory. The compound had a melting point of from 51 to 53° C.

$^1$H-NMR-spectrum: 1.31 ppm ($H_{X}$, $H_{X'}$, 2H), 1.55 ppm ($H_{Y}$, 1H), 2.79 ppm ($H_{B, HB'}$, 2H), 2.88 ppm) ($H_A$, $H_{A'}$, 2H) (AA'BB'XX'Y system), 3.70 ppm (s, 4H), 7.20–7.35 ppm (m, 10H).

$^{13}$C-NMR spectrum: 138.4 (s), 129.3 (d), 127.9 (d), 126.7 (d), 58.7 (t), 48.5 (t), 43.9 (d), 26.7 (d).

Example 14

1 g of 1-benzyl-5-chloro-4-dibenzylamino-1,2,5,6-tetrahydropyridine was triturated with 1 g of sodium borotetrahydride, and a mixture of 20 ml of acetonitrile and 2.5 ml of water was added thereto. The mixture was stirred for 4 hours at 70° C. The solvent was then removed under reduced pressure, and a mixture of 10 ml of 18% hydrochloric acid and 5 ml of acetonitrile were added to the residue, and the mixture was stirred for 2 hours at 60° C. Removal of the solvent under reduced pressure, addition of 25 ml of 4-molar potassium hydroxide solution and extraction with 4×30 ml of ether gave a crude diamine, which, after dissolution in pentane, was purified by distillation under reduced pressure in a Kugelrohr. This gave 0.5 g of the same amine as in Example 5. This corresponds to a yield of 55%.

Example 15

Ethyl 7-(1α,5α,6β-6-dibenzylamino-3-azabicyclo[3.1.0]hex-3-yl)-6-fluoro-1-(2,4difluoro-phenyl-1,4-dihydro-4-oxo-1,8-naphthyridine-3-carboxylate

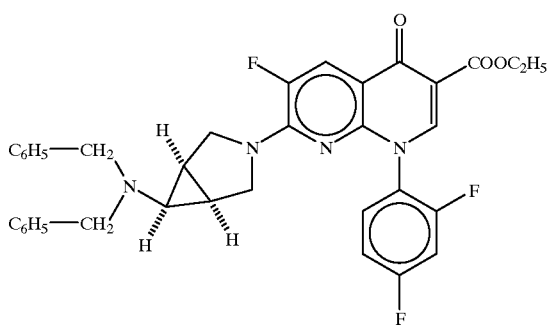

896.5 mg of ethyl 7-chloro-6-fluoro-1-(2,4-difluorophenyl)-1,4-(dihydro-4-oxo-1,8-naphthyridine-3-carboxylate were suspended in 80 ml of acetonitrile. 9.5 ml of triethylamine and 632.5 mg of 1α,5α,6β-6-dibenzylamino-3-azabicyclo[3.1.0]hexane were added and the mixture was heated for 5 hours at 60° C. The mixture was then concentrated at 60° C./20 mbar, water was added to the residue and the precipitate which formed was filtered off with suction, washed with water and dried at 70° C.

under a high vacuum. This gives 1.3 g of a crude product, which was purified by chromatography on 100 g of silica gel (Amicon, 60A 35–70 μm) using dichloromethane/methanol (95:5) as eluent.

Yield: 1.24 g (79.5% of theory), melting point 178–179° C. (with decomposition).

$^1$H-NMR (400 MHz, CF$_3$COOD): δ=1.52 (t, J=7.3 Hz, 3H), 2.20 (m, 2H), 3.06 (t, J=7.3 Hz, 1H), 3.16–3.29 (m, 1H), 3.29–3.41 (m, 1H), 3.65–3.83 (m, 2H), 4.54 (d, J=12.9 Hz, 2H), 4.71 (q, J=7.3 Hz, 2H), 4.72–4.83 (m, 2H), 7.23 (t, J=8.4 Hz, 1H), 7.32 (t, J=7.4 Hz, 1H), 7.45–7.73 (m, 11H), 8.31 (d, J=10,7 Hz, 1H), 9.14 (s, 1H).

FAB mass spectrum: m/e 625([M+H]$^+$).

Example 16

Ethyl 7-(1α,5α,6β-6-amino-3-azabicyclo[3.1.0]hex-3-yl)-6-fluoro-1-(2,4-difluoro-phenyl-1,4-dihydro-4-oxo-1,8-naphthyridine-3-carboxylate

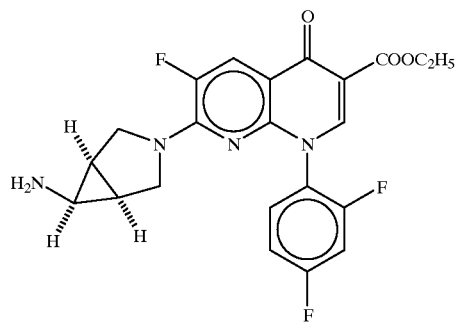

1.2 g of ethyl 7-(1α,5α,6β-6-dibenzylamino-3-azabicyclo[3.1.0]hex-3-yl)-6-fluoro-1-(2,4-difluoro-phenyl-1,4-dihydro-4-oxo-1,8-naphthyridine-3-carboxylate were dissolved in 200 ml of ethanol. 1 ml of concentrated hydrochloric acid and 100 mg of palladium/carbon (5%) were added, and the mixture was hydrogenated for 20 hours at atmospheric pressure and room temperature. A suspension formed which, together with the catalyst, was filtered off and dissolved in a mixture of dichloro-methane/methanol/17% strength ammonia (30:8:1). Undissolved catalyst was filtered off, the solution was concentrated and the residue was purified by chromatography using dichloromethane/methanol/17% strength ammonia (30:8:1) as eluent on 40 g of silica gel (Amicon, 60A 35–70 μm). The main fraction was evaporated and dried at 60° C. under a high vacuum.

Yield: 660 mg (77.3% of theory),

Melting point: 216–218° C. (with decomposition).

$^1$H-NMR (400 MHz, CDCl$_3$): δ=1.07 (broad, 2H), 1.40 (t, J=7.5 Hz, 3H), 1.66 (broad, 2H), 2.49 (t, J=6.9 Hz, 1H), 3.45–3.85 (broad, 4H), 4.38 (q, J=7.5 Hz, 2H), 7.04 (m, 2H), 7.37 (m, 1H), 8.04 (d, J=12.9 Hz, 1H), 8.36 ppm (s, 1H).

FAB mass spectrum: m/e 445 ([M+H]$^+$).

Example 17

7-(1α,5α,6β-6-Amino-3-azabicyclo[3.1.0]hex-3-yl)-6-fluoro-1-(2,4-difluoro-phenyl-1,4-dihydro-4-oxo-1,8-naphthyridine-3-carboxylic acid methane sulphonate

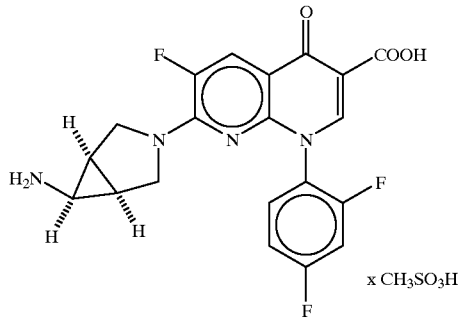

400 mg of 7-(1α,5α,6β-6-amino-3-azabicyclo[3.1.0]hex-3-yl)-6-fluoro-1-(2,4-difluoro-phenyl-1,4-dihydro-4-oxo-1,8-naphthyridine-3-carboxylate were heated to 70° C. in a mixture of 8 ml of water and 2.8 ml of 70% strength methanesulphonic acid solution for 20 hours. This gave a suspension, which was cooled in an ice bath. The precipitate was filtered off with suction, washed with ice water and dried at 80° C. in a high vacuum.

Yield: 276 mg (59.8% of theory),

Melting point: 244–247° C. (with decomposition).

$^1$H-NMR (500 MHz, CF$_3$COOD): δ=2.38 (broad, 2H), 3.1 (s, 3H), 3.28 (t, J=7.3 Hz, 1H), 3.7–4.8 (broad, 4H), 7.26 (m, 2H), 7.61 (m, 1H), 7.82 (m, 1H), 796 (broad, 3H), 8.27 (d, J=12.4 Hz, 1H), 9.21 (s, 1H).

FAB/MS: m/e 417 ([M+H]$^+$).

The prepared compound had significantly lower neurotoxicity than the corresponding exo-6-amino compound.

Although the present invention has been described in detail with reference to certain preferred versions thereof, other variations are possible. Therefore, the spirit and scope of the appended claims should not be limited to the description of the versions contained therein.

What is claimed is:

1. Endo-6-amino-3-azabicyclo[3.1.0]hexanes of the formula

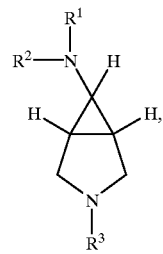

(I)

wherein

R$^1$ and R$^2$ independently of one another are a C$_3$–C$_4$-alkenyl or an Ar—CH(R')— where R' is hydrogen or a C$_1$–C$_4$-alkyl and Ar is an optionally substituted C$_6$–C$_{10}$-aryl; and R$^3$ a C$_3$–C$_4$-alkenyl, an Ar—CH(R')— wherein R' is hydrogen or a C$_1$–C$_4$-alkyl and Ar is an optionally substituted C$_6$–C$_{10}$-aryl or a COOR$^4$, in which R$^4$ is a C$_1$–C$_4$-alkyl or a C$_2$–C$_4$-alkenyl.

* * * * *